United States Patent [19]

Hatanaka

[11] Patent Number: 4,837,343
[45] Date of Patent: Jun. 6, 1989

[54] OPTICALLY ACTIVE β-AMINO ACID DERIVATIVES AND THEIR SALTS, AND PROCESSES FOR PRODUCING THE SAME

[75] Inventor: Minoru Hatanaka, Takatsuki, Japan

[73] Assignee: Kanegafuchi Kagaku Kogyo Kabushiki Kaisha, Osaka, Japan

[21] Appl. No.: 91,832

[22] Filed: Sep. 1, 1987

[30] Foreign Application Priority Data

Sep. 8, 1986 [JP] Japan ................... 61-210889

[51] Int. Cl.$^4$ ............................. C01D 309/06
[52] U.S. Cl. ................................. 549/291
[58] Field of Search ........................ 549/291

[56] References Cited

PUBLICATIONS

Heterocycles, vol. 21, pp. 29–40, (1984).
Tetrahedron Letters, vol. 26, pp. 583–586, (1985).
M. Hatanaka et al., Chemical Abstracts 108:21560w (abstract of Tennen Yuki Kagobutsu Toronkai Koen Yoshishu (1986), 28th, pp. 542–549).

*Primary Examiner*—Glennon H. Hollrah
*Assistant Examiner*—Mark W. Russell
*Attorney, Agent, or Firm*—Burgess, Ryan & Wayne

[57] ABSTRACT

Optically active β-amino acid derivatives and their salts of the following formula:

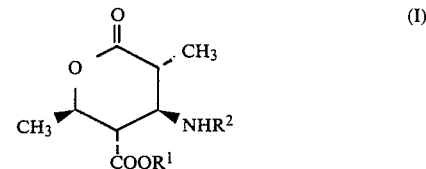

wherein $COOR^1$ is an esterified or unesterified carboxyl group; $R^2$ is hydrogen or a $C_{1-10}$ acyl or esterified carboxyl group and processes for producing the same. These compounds permit important intermediate for the synthesis of 1β-methylcarbapenem derivatives to be produced in an efficient way.

6 Claims, No Drawings

OPTICALLY ACTIVE β-AMINO ACID DERIVATIVES AND THEIR SALTS, AND PROCESSES FOR PRODUCING THE SAME

This invention relates to optically active β-amino acid derivatives and their salts, and in particular to novel, optically active (2R, 3R, 4S, 5R)-3-amino-2,5-dimethyl-5-pentanolide-4-carboxylic acid derivatives and their salts and processes for producing the same.

Carbapenem antibiotics being represented by Thienamycin, PS-5, etc. are increasingly attracting a great deal of attention because of their potent antimicrobial activity. On the other hand, these compounds suffer from some serious defects, for example, they are chemically instable and after in vivo administration, they develop nephrotoxicity through breakdown in the kidney.

Recently, it was reported that 1β-methylcarbapenem compounds derived from Thienamycin through incorporating a methyl group into the 1st position of its carbapenem skeleton can overcome the above-described defects and provide excellent characteristic properties.

With reference to the method of synthesis for such kind of compounds, there have been known, for example, the methods as described in "Heterocycles", vol. 21, pp. 29 (1984) and "Tetrahedon Letters", vol. 26 pp. 583 and 587 (1985).

Nevertheless, the above-described methods encounter great difficulties in synthesizing a given desirable stereoisomer in a stereoselective manner.

The present inventors, after intensive, repeated research work, found that the optically active compounds of the general formula I being provided with every chiralities of 1β-methylcarbapenem compounds can be synthesized with ease, and the finding has resulted in the completion of this invention. These compounds permit important intermediates for the synthesis of 1β-methylcarbapenem derivatives to be produced in the extremely efficient way. For instance, the compound (11), of which manufacturing method is shown in example 15, is an important intermediate, and from this compound is obtained a useful antibacterial agent, (−)-(1R, 5S, 6S)-6-[(1R)-1-hydroxyethyl]-1-methyl-2-(2-N,N-dimethylamino-2-iminoethylthio)-1-carbapen-2-em-3-carboxylic acid by the method described in the above-mentioned literatures.

The whole reaction pathway in accordance with this invention is given in the following.

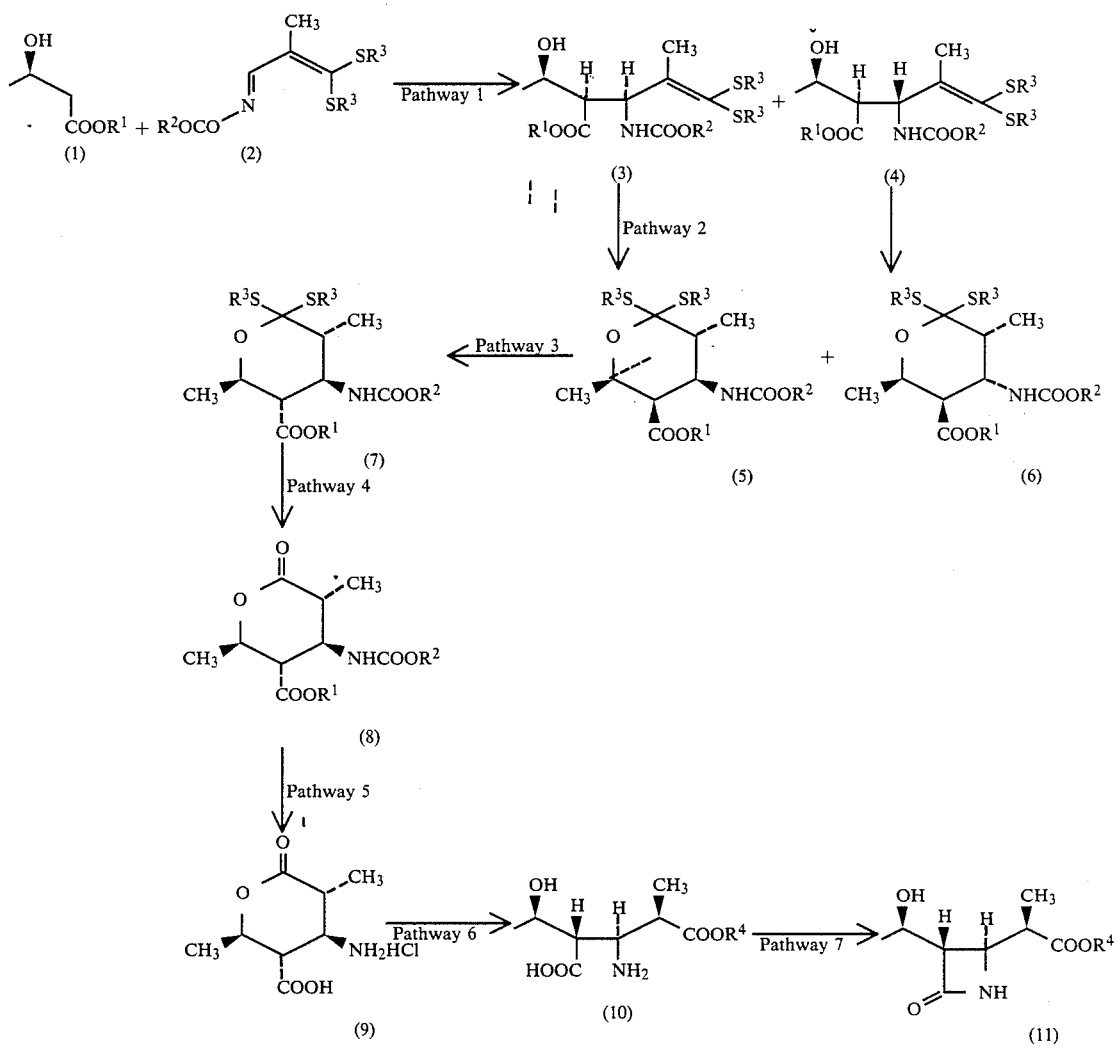

In the reaction pathway as illustrated above, examples of $R^1$, $R^2$ and $R^3$ preferably include hydrogen, straight-chain/branched or cyclic $C_{1-10}$ alkyl groups (for example, methyl, ethyl, propyl, isopropyl, butyl, sec-butyl, tert-butyl, pentyl, heptyl, cyclohexyl, etc.), aralkyl groups (for example, benzyl, phenethyl, etc.) and aryl groups (for example, phenyl, β-naphthyl, etc.).

These hydrocarbon groups may have suitable substituents (for example, carboxyl group, alkoxycarbonyl groups (exemplified by methoxycarbonyl, ethoxycarbonyl, etc.), amino group, alkyl-substituted amino groups (exemplifed by methylamino, ethylamino, diethylamino, etc.), hydroxyl group, alkoxy groups (exemplified by methoxy, ethoxy, etc.), alkylsilyl groups (exemplified by trimethylsilyl, triethylsilyl, etc.), acyloxy groups (exemplified by acetyloxy, propionyloxy, etc.), halogens (exemplified by chlorine, bromine, iodine, etc.), carbamoyl groups, mercapto groups, nitrile, nitro group, etc.], unless they cause adverse effects on the reaction.

$R^4$ is a residual group derived from an alcohol which is to be used in the alcoholysis of the compound (9), and such a group includes alkyl groups substituted or not substituted by halogens, such as methyl, ethyl and trichloroethyl; and aralkyl groups, such as benzyl group, with their numbers of carbon atoms being preferably in the range of 1 to 10.

The invention described herein covers optically active β-amino acid derivatives of the following formula:

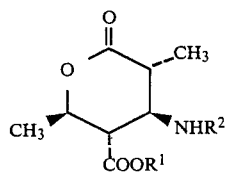
(I)

wherein $COOR^1$ is an esterified or unesterified carboxyl group; $R^2$ is hydrogen or a $C_{1-10}$ acyl or esterified carboxyl group and their salts.

This invention comprehends the compounds (8) and (9) in the reaction pathway as illustrated above.

As salts of the compounds of the present invention, when $R^1$ is H, sodium salts, potassium salts may be obtained, and when $R^2$ is H, hydrochlorides and sulfates may be obtained, for instance.

The invention also constitutes a process for producing optically active β-amino acid derivatives of the formula:

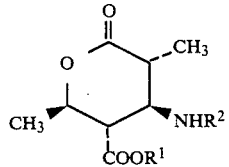
(I)

wherein $COOR^1$ and $R^2$ are as defined hereinbefore and their salts, characterized in that said process comprises treating a compound of the following formula:

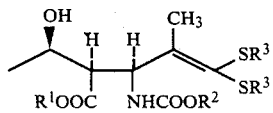
(3)

wherein $COOR^1$ and $R^2$ are as defined hereinbefore; $SR^3$ is a protected or unprotected mercapto group with an acid to give a compound of the following formula:

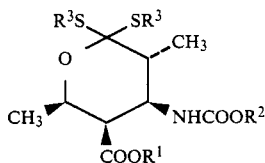
(5)

wherein $COOR^1$ and $R^2$ are as defined hereinbefore and allowing a base to act on the same to give a compound of the following formula:

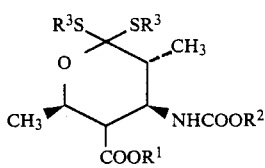
(7)

wherein $COOR^1$, $R^2$ and $SR^3$ are as defined hereinbefore through inversion of a substituent configuration in the 5th position followed by reaction with an inorganic salt or halogenating agent.

(Pathway 2)

The conversion of (3) to (5) is carried out by treating the former with one hundredth to twice as much as an acid, such as sulfuric acid, hydrochloric acid, perchloric acid, trifluoroacetic acid and p-toluenesulfonic acid, in such a solvent as dichloromethane, dichloroethane, chloroform, benzene, ethyl acetate, ether and THF at a temperature ranging from 0° C. to 50° C.

When a mixture of (3) and (4) is subjected to a reaction under the same conditions, there results a mixture of (5) and (6). Separatory purification of the resulting mixture for (5) is easily performed by column chromatography.

(Pathway 3)

The conversion of (5) to (7) is carried out by treating the former in a solvent, such as lower alcohols being exemplified by methanol, ethanol and t-butanol, aqueous acetone, acetonitrile and THF, in the presence of such a base as sodium carbonate, potassium carbonate, sodium hydroxide, potassium hydroxide, sodium methylate, sodium ethylate and potassium t-butoxide at a temperature ranging from 25° C. to 100° C. for 10 minutes to 24 hours.

Similar treatment of a mixture of (5) and (6) also yields a mixture of (7) and unreacted (6). Separatory purification of the resulting mixture is easily performed by column chromatography and the like.

(Pathway 4)

The conversion of (7) to (8) is conducted by means of the methods (for example, the method described in Greene; "Protective Groups in Organic Synthesis", pp. 129-139) being conventionally employed for the conversion of dithioacetal to carbonyl compounds. Typically, the conversion is carried out through treatment with a combination of inorganic salts, such as $CuCl_2$ and CuO, $AgNO_3$ and $Ag_2O$ and $HgCl_2$ and HgO, or a halogenating agent, such as bromine, N-bromosuccinimide, N-chlorosuccinimide and 1,3-dibromo-5,5-dimethylhydantoin, in such a solvent as acetone, acetonitrile, THF and alcohols being exemplified by methanol, after being admixed with a small amount or 70% of water, at a temperature ranging from 0° C. to 100° C. for 5 minutes to 24 hours.

(Pathway 5)

The conversion of (8) to (9) is carried out by treating the former with an acid such as hydrochloric acid and sulfuric acid in an aqueous solution at a temperature ranging from 20° C. to 100° C. for 1 to 48 hours.

(Peripheral Pathway)

(1) and (2) are converted to (3) and (4), for example, by the following procedure; namely, (R)-3-hydroxybutyrate (1) (wherein Ester moiety $R^1$ is as defined hereinbefore) is treated with twice to 2.5 times as much as a lithium introducing agent, such as lithium diisopropylamide, lithium bis(trimethylsilyl)amide, lithium N-t-butylcyclohexylamide and lithium 2,2,6,6-tetramethylpiperide, in a dried solvent, such as ether, THF, 1,2-dimethoxyethane and dioxane at a temperature ranging from −78° C. to 0° C. for 10 minutes to 5 hours, followed by treatment at a temperature ranging from −78° C. to 0° C. for 10 minutes to 5 hours with a solution in the same solvent as used in the reaction, e.g. THF, of one equivalent of the compound (2) (wherein $R^2$ and $R^3$ are as defined hereinbefore) as prepared by the method to be described below.

The product is a mixture consisting of two kinds of the isomers, (3) and (4), and these two compound can be separated by column chromatography. Since the desirable isomer alone can be readily separated and purified in the subsequent step for the production of (7) or (8), however, (3) and (4) can be employed in the form of a mixture without being separated in the following step.

Production of the compound (2):

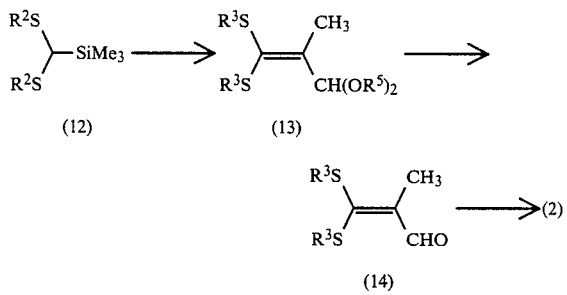

The compound (2) can be produced from (12) via (13) and (14) in the three steps. In the first place, the conversion of (12) to (13) is carried out by treating the compound (12) (wherein $R^3$ is as defined hereinbefore) with once to 1.2 times as much as a lithium introducing agent, such as n-butyllithium and lithium diisopropylamide, in a dried solvent, such as ether and THF, at a temperature ranging from −78° C. to 30° C. for 1 to 48 hours, followed by treatment with one to 1.5 times as much as pyruvic aldehyde acetal of $CH_3COCH(OR^5)_2$ [wherein $R^5$ is an alkyl group of 1 to 10 carbon atoms] at a temperature ranging from −78° C. to 30° C. for 1 to 48 hours.

The conversion of (13) to (14) is conducted by treatment in a solvent, such as alcohols with a water content of 1 to 80% being exemplified by methanol and ethanol, acetone, THF and dioxane, in the presence of such an acid as hydrochloric acid, sulfuric acid, phosphoric acid, perchloric acid, acetic acid, trifluoroacetic acid and p-toluenesulfonic acid at a temperature ranging from 0° C. to 60° C. for 10 minutes to 48 hours. Alternatively, the conversion can be performed by dissolving the compound (13) in a solvent, such as dichloromethane, chloroform, benzene, ethyl acetate and ether, followed by stirring with a 1 to 60% aqueous solution of the above-described acid at 0° C. to room temperature for 10 minutes to 48 hours.

The conversion of (14) to (2) is carried out by treating hexamethyldisilazane and n-butyllithium in such a solvent as ether, THF, hexane and pentane at a temperature ranging from −78° C. to 25° C. for 10 minutes to 24 hours in accordance with the conventional method, then treating the thus-prepared solution of lithium bis(trimethylsilyl)amide with one equivalent of (14) at a temperature ranging from −78° C. to 30° C. for 10 minutes to 24 hours and then stirring with one to two times as much as chlorotrimethylsilane admixed at a temperature ranging from −78° C. to 40° C. for 30 minutes to 48 hours, followed by treatment with one to two times as much as $R^2COCl$ [wherein $R^2$ is as defined herein before] at a temperature from −78° C. to 30° C. for 10 minutes to 48 hours.

Also, the desired (2) can be obtained by utilizing twice to three times as much as $R^2OCOCl$ without adding the above mentioned chlorotrimethylsilane.

The conversion of (9) to (10) is carried out by treating the former with an alcohol such as methanol, ethanol, benzyl alcohol, phenol and 2,2,2-trichloroethanol at a temperature ranging from 20° C. to 100° C. for 1 to 24 hours.

Esterified portion $R^4$ in the compound (10) may be the same one as in the alcohol $R^4OH$ used in the conversion of (9) to (10).

The conversion of (10) to (11) is carried out by treating the former with dicyclohexylcarbodiimido (DCC) in the presence of a base such as triethylamine, pridine, dimethylaniline and 4-dimethylaminopyridine, or an oxide such as ethylene oxide and propylene oxide in a solvent such as alcohol being exemplified by methanol and ethanol, or acetonitrile at a temperature ranging from 20° C. to 100° C.

The following examples are further illustrative of the present invention.

EXAMPLE 1

Production of 2-(1,3-dithian-2-yliden) propanol dimethylacetal [13; $R^3$=—$(CH_2)_3$—, $R^5$=$CH_3$]

A solution of 35.2 g of 2-trimethylsilyl-1,3-dithian in 400 ml of anhydrous THF was cooled to −78° C., and n-butyllithium (0.195 mol)-hexane solution was added dropwise to the solution under stream of argon, whereby care was taken to maintain it at a temperature of below −60° C. After completion of the addition, the reaction solution was raised gradually to 0° C. over the period of 4 hours and then cooled again to −78° C., and 23.54 ml of pyruvic aldehyde dimethylacetal was gradually added dropwise to it below −60° C. After stirring was continued at the same temperature for 1 hour, the reaction solution was left on standing overnight at room temperature and poured into a mixture of 300 ml of methylene chloride and 300 ml of water, followed by thorough shaking. The methylene chloride layer was separated, dried (over $MgSO_4$) and concentrated under reduced pressure. The residue was distilled under reduced pressure to give 35.7 g of the desired compound.

bp. 105°–110° C./0.1 mmHg $^1$H-NMR ($CDCl_3$) δ, 1.68(3H, s), 2.08(2H, m), 2.79(4H, m), 8.20(6H, s), 5.21(1H, s).

EXAMPLE 2

Production of 2-(1,3-dithian-2-yliden)propanol [14; $R^3 = -(CH_2)_3-$]

In 80 ml of chloroform was dissolved 19.0 g of 2-(1,3-dithian-2-yliden)propanal dimethylacetal [13; $R^3 = -(CH_2)_3-$, $R^5 = CH_3$], and 40 ml of a 1:1 mixture of trifluoroacetic acid and water was added to the solution under ice cooling, followed by stirring at the same temperature for 2 hours. The chloroform layer was separated, washed with water, aqueous sodium hydrogencarbonate solution and water successively and concentrated under reduced pressure. The residue was crystallized from isopropyl etherhexane to give 13.1 g of the desired compound.

mp., 80°-82° C.

Elemental analysis, for $C_7H_{10}OS_2$: Calcd: C, 48.24; H, 5.78; S, 36.79 Found: C, 48.13; H, 5.49; S, 36.55.

$^1$H-NMR (CDCl$_3$) δ, 1.23(3H, s), 2.16(2H, m), 2.92(4H, m), 9.96(1H, s).

EXAMPLE 3

Production of N-methoxycarbonyl-2-(1,3-dithian-2-yliden)propanimine [2; $R^2 = CH_3$, $R^3 = -(CH_2)_3-$]

A solution of 9.8 ml of 1,1,1,3,3,3-hexamethyldisilazane in 50 ml of anhydrous THF was cooled to −78° C., and 30 ml of 1.5M n-butyllithium-hexane solution was added dropwise to the solution. After stirring was continued at the same temperature for 1 hour, a solution of 7.37 g of 2-(1,3-dithian-2-yliden)propanal [14; $R^3 = -(CH_2)_3-$] in 30 ml of anhydrous THF was gradually added dropwise to the solution below −60° C., and stirring was continued at −78° C. for another hour. After addition of 6.44 ml of chlorotrimethylsilane, the reaction solution was gradually warmed up to room temperature and then ice-cooled. To it was added 3.92 ml of methyl chloroformate gradually and dropwise. The reaction solution was left overnight in a refrigerator and concentrated to dryness under reduced pressure. The residue was extracted with methylene chloride. The extract was concentrated under reduced pressure to give 8.92 g of the objective compound in the form of crystals.

mp., 89°-91° C.

Elemental analysis, for $C_9H_{13}NO_2S_2$: Calcd.: C, 46.73; H, 5.66; N, 6.05; S, 27.72 Found: C, 46.60; H, 5.42; N, 5.97; S, 28.00.

IR (CH$_2$Cl$_2$), 1700, 1565 cm$^{-1}$.

$^1$H-NMR (CDCl$_3$) δ, 2.07(3H, s), 2.10(2H, m), 3.07(4H, m), 3.87(3H, s), 9.34(1H, s).

EXAMPLE 4

Production of methyl 4-(1,3-dithian-2-yliden)-2-(R)-(1-(R)-hydroxyethyl)-3-(R,S)-methoxycarbonylaminopentanoate [3; $R^1 = R^2 = CH_3$, $R^3 = -(CH_2)_3-$] and [4; $R^1 = R^2 = CH_3$, $R^3 = -(CH_2)_3-$]

A solution of anhydrous THF (100 ml) containing 0.042 mol of lithium diisopropylamide (prepared from n-butyllithium and diisopropylamide in accordance with the conventional method) was cooled to −78° C., and 2.36 g of methyl (R)-3-hydroxybutyrate was added dropwise to it under a stream of argon. After stirring was continued at the same temperature for 1 hour, a solution of 4.62 g of N-methoxycarbonyl-2-(1,3-dithian-2-yliden)propanimine [2; $R^2 = CH_3$, $R^3 = -(CH_2)_3-$] in 100 ml of anhydrous THF was gradually added to dropwise to the mixed solution, and stirring was continued at −78° C. for 1 hour. After addition of 2.4 ml of acetic acid, the reaction solution was poured into 100 ml of water, and was extracted with ethyl acetate. The extract was washed with water, dried (over MgSO$_4$) and concentrated under reduced pressure. The residue was purified by silica-gel column chromatography, and the eluate with benzene-ethyl acetate (7:1) yielded 1.89 g of the desired compound [4; $R^1 = R^2 = CH_3$, $R^3 = -(CH_2)_3-$];

$^1$H-NMR (CDCl$_3$) δ, 1.22(3H, d, J=7.0 Hz), 1.62(3H, s), 2.02 (2H, m), 2.47(1H, m), 2.82(4H, m), 3.56(3H, s), 3.61(3H, s), 3.82(1H, m), 5.27(1H, dd, J=9.0, 6.0 Hz), 5.96(1H, d, J=9.0 Hz)

and 4.74 g of the object compound [3; $R^1 = R^2 = CH_3$, $R^3 = -(CH_2)_3-$];

$^1$H-NMR (CDCl$_3$) δ, 1.15(3H, d, J=6.7 Hz), 1.76(3H, s), 2.02 (2H, m), 2.76(3H, m), 3.57(3H, s), 3.58(3H, s), 3.85(1H, m), 5.45(1H, t, J=9.0 Hz), 5.96(1H, d, J=9 Hz), both in the form of an oily substance.

EXAMPLE 5

Production of (3R, 4S, 5R, 6R)-3,6-dimethyl-5-methoxycarbonyl-4-methoxycarbonylaminotetrahydropyran-2-spiro-2'-(1',3'-dithian) [5; $R^1 = R^2 = CH_3$, $R^3 = -(CH_2)_3-$]

In 100 ml of methylene chloride was dissolved 3.49 g of methyl 4-(1,3-dithian-2-yliden)-2-(R)-(1-(R)-hydroxyethyl)-3-(S)-methoxycarbonylaminopentanoate [3; $R^1 = R^2 = CH_3$, $R^3 = -(CH_2)_3-$], and 10 ml of 0.1M HCl-methylene chloride solution was added to the solution, followed by stirring under ice-cooling for 2 hours. The reaction solution was washed with aqueous sodium hydrogen carbonate solution and concentrated under reduced pressure, and the residue was crystallized from isopropyl ether to give 3.20 g of the desired compound.

mp., 72°-74° C.

$[\alpha]_D^{29} + 166°$ (c=1.0, MeOH).

IR (CH$_2$Cl$_2$) 3450, 1730, 1512 cm$^{-1}$.

$^1$H-NMR (CDCl$_3$) δ 11.19(3H, d, J=6.9 Hz), 1.34(3H, d, J=6.6 Hz), 1.87–2.10(2H, m), 2.63(2H, m), 2.65(1H, dq, J=11.5, 6.9 Hz), 2.90(1H, m), 2.94(1H, dd, J=4.8, 3.8 Hz), 3.49(1H, m), 3.66 (3H, s), 3.73(3H, s), 4.00(1H, m), 4.44(1H, m), 4.88(1H, d, J=9.8 Hz).

EXAMPLE 6

Production of (3R, 4S, 5S, 6R)-3,6-dimethyl-5-methoxycarbonyl-4-methoxycarbonylaminotetrahydropyran-2-spiro-2'-(1',3'-dithian) [7; $R^1 = R^2 = CH_3$, $R^3 = -(CH_2)_3-$]

In 100 ml of anhydrous methanol was dissolved 1.75 g of (3R, 4S, 5R, 6R)-3,6-dimethyl-5-methoxycarbonyl-4-methoxycarbonylaminotetrahydropyran-2-spiro-2'-(1',3'-dithian) [5; $R^1 = R^2 = CH_3$, $R^3 = -(CH_2)_3-$], and 10.5 ml of 1M sodium methylate-methanol solution was added to the solution, and the mixture was heated under reflux for 8 hours. The solution was allowed to cool and admixed with 2.4 ml of acetic acid, and the solvent was distilled off under reduced pressure. The residue was dissolved in a mixture of 50 ml of methylene chloride and 20 ml of water, and the methylene chloride layer was washed with water, dried (over MgSO$_4$) and concentrated under reduced pressure. The residue was crystallized from isopropyl ether to give 1.36 g of the objective compound.

mp., 155°–156° C.

$[\alpha]_D^{29}$ +114° (c=1.0, MeOH).

Elemental analysis, for $C_{14}H_{23}NO_5S_2$ Calcd.: C, 48.12; H, 6.63; N, 4.01; S, 18.35; Found: C, 48.04; H, 6.62; N, 4.01; S, 18.14.

IR ($CH_2Cl_2$) 3440, 1740, 1515 cm$^{-1}$.

$^1$H-NMR (CDCl$_3$) δ 1,21(3H, d, J=6.8 Hz), 1.29(3H, d, J=6.15 Hz), 1.80–2.12(3H, m), 2.41(1H, dd, J=10.3, 10.8 Hz), 2.65(2H, m), 2.94(1H, m), 3.48(1H, m), 3.70(6H, s), 4.05(1H, ddd, J=10.4, 10.5, 10.8 Hz), 4.32(1H, dq, J=10.3, 6.15 Hz), 4.65(1H, d, J=10.4 Hz).

EXAMPLE 7

Production of methyl (2R, 3R, 4S, 5R)-2,5-dimethyl-3-methoxycarbonylamino-5-pentanolide-4-carboxylate [8; $R^1=R^2=CH_3$]

In 50 ml of acetone was dissolved 1.70 g of (3R, 4S, 5S, 6R)-3,6-dimethyl-5-methoxycarbonyl-4-methoxycarbonylaminotetrahydropyran-2-spiro-2'-(1',3'-dithian) [7; $R^1=R^2=CH_3$, $R^3=-(CH_2)_3-$], and 1.66 g of cupric chloride dihydrate and 1.55 g of cupric oxide were added to the solution, and the mixture was heated under reflux with stirring for 2 hours. The reaction solution was cooled with ice, and the insoluble matter was removed by filtration, whereupon the filtrate was concentrated under reduced pressure. The residue was purified by silica-gel column chromatography, and the eluate with chloroform-methanol (15:1) yielded 1.01 g of the desired compound in the form of crystals.

mp., 135°–137° C.

$[\alpha]_D^{29}$ +31.4° (c=1.1, CHCl$_3$).

Elemental analysis, for $C_{11}H_{17}NO_6$: Calcd.: C, 50.96; H, 6.61; N, 5.40; Found: C, 50.70; H, 6.31; N, 5.32.

IR ($CH_2Cl_2$) 3440, 1740, 1515 cm$^{-1}$.

$^1$H-NMR (CDCl$_3$) δ 1,38(3H, d, J=6.2 Hz), 1.39(3H, d, J=7.1 Hz), 2.67(1H, m), 2.84(1H, dd, J=10.5, 109 Hz), 3.75(6H, s), 3.93 (1H, ddd, J=10.9, 10.7, 9.1 Hz), 4.54(1H, dq, J=10.5, 6.2 Hz).

EXAMPLE 8

Production of N-benzyloxycarbonyl 2-(1,3-dithian-2-yliden)propanimine [2: $R^2=CH_2C_6H_5$, $R^3=-(CH_2)_3-$]

By following the same procedure as described in Example 3, the reaction was carried out with use of benzyl chloroformate in place of methyl chloroformate to give the desired compound in excellent yield.

mp., 85°–88° C.

IR ($CH_2Cl_2$) 1705, 1565 cm$^{-1}$.

$^1$H-NMR (CDCl$_3$) δ 2.07(3H, s), 2.20(2H, m), 3.05(4H, m), 5.28 (2H, s), 7.43(5H, s), 9.34(1H, s).

EXAMPLE 9

Production of methyl 3-(R,S)-benzyloxycarbonylamino-4-(1,3-dithian-2-yldien)-2-(R)-(1-(R)-hydroxyethyl)pentanoate [3; $R^1=CH_3$, $R^2=CH_2C_6H_5$, $R^3=-(CH_3)-$] and [4; $R^1=CH_3$, $R^2=CH_2C_6H_5$, $R^3=-(CH_2)_3-$]

By following the same procedure as described in Example 4, the reaction was conducted with use of N-benzyloxycarbonyl 2-(1,3-dithian-2-yliden)propanimine [2; $R^2=CH_2C_6H_5$, $R^3=-(CH_2)_3-$] in place of N-methoxycarbonyl 2-(1,3-dithian-2-yliden)propanimine [2; $R^2=CH_3$, $R^3=-(CH_2)_3-$] to give the objective compound in the form of an oily substance.

IR ($CH_2Cl_2$) 3440, 1725, 1500 cm$^{-1}$.

EXAMPLE 10

Production of (3R, 4S, 5R, 6R)- and (3R, 4R, 5R, 6R)-4-benzyloxycarbonylamino-3,6-dimethyl-5-methoxycarbonyltetrahydropyran-2-spiro-2'-(1',3'-dithian) [5; $R^1=CH_3$, $R^2=CH_2C_6H_5$, $R^3=-(CH_2)_3-$] and [6; $R^1=CH_3$, $R^2=CH_2C_6H_5$, $R^3=-(CH_2)_3-$]

In 200 ml of methylene chloride was dissolved 6.5 g of methyl 3-(R,S)-benzyloxycarbonylamino-4-(1,3-dithian)-2-yliden)-2-(R)-(1-(R)-hydroxyethyl)-pentanoate as obtained in Example 9, and 0.1 ml of 5.2M hydrogen chloride-dioxane solution was added to the solution, followed by stirring at room temperature for 2 hours. The reaction solution was washed with aqueous sodium hydrogen carbonate solution and concentrated under reduced pressure, and the oily residue was purified by silica-gel column chromatography. The eluate with benzene-ethyl acetate (15:1) yielded 1.63 g of the desired compound [6; $R^1=CH_3$, $R^2=CH_2C_6H_5$, $R^3=-(CH_2)_3$];

$^1$H-NMR (CDCl$_3$) δ 1.17(3H, d, J=6.9 Hz), 1.33(3H, d, J=6.6 Hz), 1.86–2.08(2H, m), 2.56–2.69(3H, m), 2.88(1H, m), 2.95(1H, dd, J=3.4, 4.8 Hz), 3.47(1H, m), 3.47(1H, m), 3.68(3H, s), 4.08 (1H, m), 4.43(1H, m), 5.08(2H, s), 7.34(5H, m), and 4.15 g of the same [5; $R^1=CH_3$, $R^2=CH_2C_6H_5$, $R^3=-(CH_2)_3-$];

IR ($CH_2Cl_2$) 3400, 1735, 1720(sh), 1510 cm$^{-1}$.

$^1$H-NMR (CDCl$_3$) δ 1.17(3H, d, J=7.2 Hz), 1.38(3H, d, J=6.6 Hz), 1.80–2.07(2H, m), 2.60(3H, m), 2.85(1H, m), 3.00(1H, m), 3.53(1H, m), 3.72(3H, s), 4.13(1H, m), 4.29(1H, m), 5.10(2H, dd, J=1.22, 18.2 Hz), 7.35(5H, m).

EXAMPLE 11

Production of (3R, 4S, 5S, 6R)-4-benzyloxycarbonylamino-3,6-dimethyl-5-methoxycarbonyl-tetrahydropyran-2-spiro-2'-(1',3'-dithian) [7; $R^1=CH_3$, $R^2=CH_2C_6H_5$, $R^3=-(CH_2)_3-$]

By following the same procedure as described in Example 6, (3R, 4S, 5R, 6R)-4-benzyloxycarbonylamino-3,6-dimethyl-5-methoxycarbonyl-tetrahydrohydropyran-2-spiro-2'-(1',3'-dithian) [5; $R^1=CH_3$, $R^2=CH_2C_6H_5$, $R^3=-(CH_2)_3-$] was reacted with sodium methylate to give the desired compound in yield of 85%.

The crystals showed the following physical properties:

mp., 145°–146° C.

$[\alpha]_D^{29}$ +81.7° (c=0.85, MeOH).

IR ($CH_2Cl_2$) 3440, 1740, 1515 cm$^{-1}$.

$^1$H-NMR (CDCl$_3$) δ1.21(3H, d, J=6.8 Hz), 1.28(3H, d, J=6.2 Hz), 1.75–2.11(3H, m), 2.39(1H, dd, J=10.6, 10.8 Hz), 2.65(2H, m), 2.92(1H, m), 3.47(1H, m), 3.60(3H, s), 4.08(1H, ddd, J=9.6, J=9.6, 10.8, 11.1 Hz), 4.32(1H, m), 4.63(1H, d, J=9.6 Hz), 5.07(2H, dd, J=16.0, 12.3 Hz), 7.35(5H, m).

EXAMPLE 12

Production of methyl (2R, 3R, 4S, 5R)-3-benzyloxycarbonylamino-2,5-dimethyl-5-pentanolide-4-carboxylate [8; $R^1=CH_3$, $R^2=CH_2C_6H_5$]

By following the same procedure as described in Example 7, the objective compound was prepared in yield of 86% from (3R, 4S, 5S, 6R)-4-benzyloxycarbonylamino-3,6-dimethyl-5-methoxycarbonyl-tetrahydropyran-2-spiro-2'-(1',3'-dithian) [7; $R^1=C_3$, $R^2=CH_2C_6H_5$, $R^3=-(CH_2)_3-$].

mp., 143°–145° C.

$[\alpha]_D^{29}+22.4°$ (c1.35, $CHCl_3$).

Elemental analysis, for $C_{17}H_{21}NO_6$: Calcd.: C, 60.88; H, 6.31; N, 4.18; Found: C, 60.67; H, 6.05; N, 4.31.

IR ($CH_2Cl_2$) 3440, 1740, 1515 cm$^{-1}$.

$^1$H-NMR ($CDCl_3$) δ 1.37(3H, d, J=6.1 Hz), 1.39(3H, d, J=6.9 Hz), 2.66(1H, m), 2.83(1H, t, J=10.9 Hz), 3.63(3H, s), 3.92(1H, ddd, J=11.0, 10.9, 9.0 Hz), 4.53(1H, m), 4.89(1H, d, J=9.0 Hz), 5.10 (2H, s), 7.35(5H, m).

EXAMPLE 13

Production of (2R, 3R, 4S, 5R)-3-amino-2,5-dimethyl-5-pentanolide-4-carboxylic acid (9)

A mixture of 670 mg of methyl (2R, 3R, 4S, 5R)-3-benzyloxycarbonylamino-2,5-dimethyl-5-pentanolide-4-carboxylate [8; $R^1=CH_3$, $R^2=CH_2C_6H_5$] in 15 ml of concentrated hydrochloric acid was stirred overnight. The reaction solution was concentrated to dryness under reduced pressure, and the residue was dried in a vacuum desiccator at a temperature of 50° C. to give 430 mg of hydrochloride of the desired compound in the form of crystals. The crystals showed the following physical properties.

mp., 160°–163° C. (decomp.)

Elemental analysis, for $C_8H_{14}NO_4Cl$ Calcd.: C, 42.96; H, 6.31; N, 6.26; Found: C, 42.86; H, 6.60; N, 5.98.

EXAMPLE 14

Production of methyl (2R, 3R, 4S, 5R)-3-amino-4-carboxy-5-hydroxy-2-methyl-hexanoate (10; $R^4=CH_3$)

In anhydrous methanol was dissolved 430 mg of hydrochloride of (2R, 3R, 4S, 5R)-3-amino-2,5-dimethyl-5-pentanolide-4-carboxylic acid (9), and the solution was left on standing overnight. The solvent was distilled off under reduced pressure to give the hydrochloride of the desired compound, which exhibited the following absorption peaks in the $^1$H-NMR spectrophotometry.

$^1$H-NMR ($CDCl_3$-DMSO $d_6$) δ 1.35(3H, d, J=6.2 Hz), 1.42(3H, d, J=7.0 Hz), 2.56(1H, m), 3.22(1H, m), 3.72(3H, s), 4.10(1H, m), 4.45(1H, m).

EXAMPLE 15

Production of methyl 2(R)-[(3S, 4R)-3-(1(R)-hydroxyethyl)-2-oxoazetidine-4-yl]propanoate (1; $R^4=CH_3$)

In 30 ml of anhydrous methanol was dissolved 510 mg of the hydrochloride of methyl (2R, 3R, 4S, 5R)-3-amino-4-carboxy-5-hydroxy-2-methyl-hexanoate (10), and 1 ml of propene oxide was added to the solution, and the mixture was heated under reflux for 10 minutes. The solution was allowed to cool and admixed with 450 mg of DCC, and the mixture was heated with stirring at 50° C. for 4 hours. The solvent was distilled off under reduced pressure, and the residue was extracted with ethyl acetate. The extract was freed of the insoluble matter by filtration and concentrated under reduced pressure, and the residue was purified by silica-gel column chromatography. The eluate with benzene-ethyl acetate (1:1) yielded 310 mg of the desired compound.

The objective compound showed the following physical properties.

mp., 102°–104° C.

Elemental analysis, for $C_6H_{15}NO_4$: Calcd.: C, 53.72; H, 7.51; N, 6.96; Found: C, 53.44; H, 7.27; N, 6.93.

$[\alpha]_D^{24}-44.7°$ (c=0.45, $CHCl_3$).

IR ($CH_2Cl_2$) 3410, 1768, 1735 cm$^{-1}$.

$^1$H-NMR ($CDCl_3$) δ 1.27(3H, d, J=7.1 Hz), 1.31(3H, d, J=6.3 Hz), 2.67(1H, m), 2.98(1H, dd, J=2.1, 7.0 Hz), 3.72(3H, s), 3.77 (1H, dd, J=2.1, 7.7 Hz), 4.16(1H, m), 6.09(1H, broad s).

EXAMPLE 16

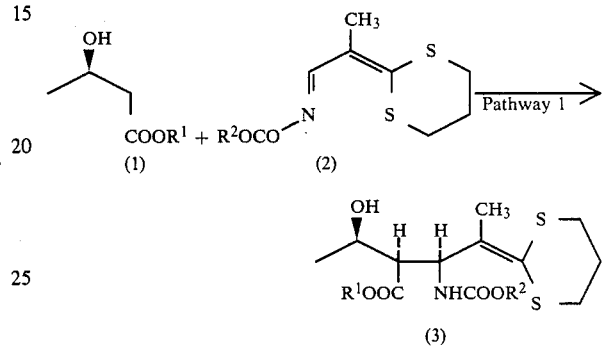

By following the same procedure as described in Example 4, but using t-butyl, i-propyl and β-naphthyl as $R^1$, and methyl and benzyl as $R^2$, the above compounds (3) were obtained. The results are shown in the following Table 1.

TABLE 1

| $R^1$ | $R^2$ | yield | (2R,3S)/(2R,3R) molar ratio of the compounds (3) |
|---|---|---|---|
| t-butyl | benzyl | 66% | 2.0 |
| t-butyl | methyl | 65% | 1.8 |
| i-propyl | methyl | 70% | 2.0 |
| β-naphtyl | methyl | 10% | 14 |

Structures of the obtained compounds were confirmed by leading to the compounds (9) through the pathway 2 to 5.

I claim:

1. Optically active β-amino acid derivatives of the following formula:

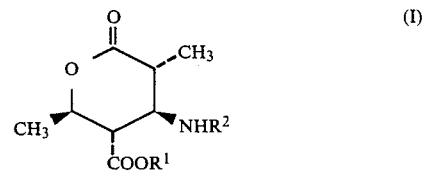

wherein $R^1$ and $R^2$ are selected from the group consisting of hydrogen, methyl, ethyl, propyl, isopropyl, butyl, sec-butyl, tert-butyl, pentyl, heptyl, cyclohexyl, benzyl, phenethyl, phenyl, β-naphthyl, carboxyl, methoxycarbonyl, ethoxycarbonyl, methylamino, ethylamino, diethylamino, methoxy, ethoxy, trimethylsilyl, triethylsilyl, acetyloxy, propionyloxy, chlorine, bromine, iodine, carbamoyl, mercapto, nitrile and nitro, and salts of said derivatives wherein the salts are sodium or potassium when $R^1$ is hydrogen and the salts are hydrochlorides or sulfates when $R^2$ is hydrogen.

2. The derivative of claim 1 wherein $R^1$ is selected from the group consisting of methyl, t-butyl, isopropyl and β-naphthyl, and $R^2$ is methyl or benzyl.

3. The derivative of claim 1 wherein $R^1$ is methyl and $R^2$ is methyl or benzyl.

4. Methyl (2R, 3R, 4S, 5R)-3-benzyloxycarbonylamino-2,5-dimethyl-5-pentanolide-4-carboxylate.

5. (2R, 3R, 4S, 5R)-3-amino-2,5-dimethyl-5-pentanolide-4-carboxylic acid.

6. Methyl (2R, 3R, 4S, 5R)-3-methoxycarbonylamino-2,5-dimethyl-5-pentanolide-4-carboxylate.

* * * * *

Notice of Adverse Decisions in Interference

In Interference No. 102,470, involving Patent No. 4,837,343, M. Hatanaka, OPTICALLY ACTIVE BETA-AMINO ACID DERIVATIVES AND THEIR SALTS, AND PROCESSES FOR PRODUCING THE SAME, final judgment adverse to the patentee was rendered Apr. 18, 1991, as to claims 1-6.
*(Official Gazette September 3, 1991.)*